United States Patent [19]

Matsui et al.

[11] Patent Number: 4,496,586
[45] Date of Patent: Jan. 29, 1985

[54] CYCLOPROPANECARBOXYLATES, THEIR PRODUCTION AND INSECTICIDE CONTAINING THEM AS AN ACTIVE INGREDIENT

[75] Inventors: Masanao Matsui; Liau Chun-Eng, both of Tokyo; Kunio Kogami, Machida; Toshihiko Yano, Ikoma; Noritada Matsuo, Itami, all of Japan

[73] Assignee: Sumitomo Chemical Company, Limited, Osaka, Japan

[21] Appl. No.: 543,226

[22] Filed: Oct. 20, 1983

Related U.S. Application Data

[63] Continuation of Ser. No. 306,376, Sep. 28, 1981, Pat. No. 4,496,586.

[30] Foreign Application Priority Data

Oct. 9, 1980 [JP] Japan .................................. 55-141799
Dec. 19, 1980 [JP] Japan .................................. 55-181012
Dec. 19, 1980 [JP] Japan .................................. 55-181013

[51] Int. Cl.$^3$ .................. C07C 69/747; C07C 69/743
[52] U.S. Cl. ...................................... 514/531; 560/124
[58] Field of Search ................. 560/124; 424/305, 306

[56] References Cited

U.S. PATENT DOCUMENTS

| | | | |
|---|---|---|---|
| 2,603,652 | 7/1952 | Schechter et al. | |
| 3,636,059 | 1/1972 | Matsui | 560/124 |
| 3,876,681 | 4/1975 | Okuno | 560/124 |
| 4,024,163 | 5/1977 | Elliott | 560/124 |

FOREIGN PATENT DOCUMENTS

| | | | |
|---|---|---|---|
| 2290415 | 9/1976 | France | |
| 50-3369 | 2/1975 | Japan | 560/124 |
| 52-45768 | 11/1977 | Japan | 424/306 |
| 56-57737 | 5/1981 | Japan | 560/124 |
| 1158964 | 7/1969 | United Kingdom | 560/124 |

OTHER PUBLICATIONS

Elliott, Chem. Soc. Rev., vol. 7, pp. 473–505, (1978).

Primary Examiner—Michael L. Shippen
Attorney, Agent, or Firm—Stevens, Davis, Miller & Mosher

[57] ABSTRACT

The present invention relates to carboxylic acid esters of the formula (I),

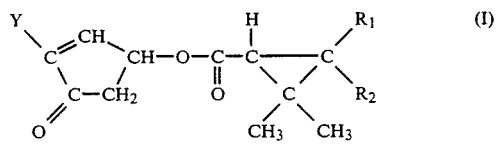

wherein $R_1$ is a hydrogen atom or a methyl group, and when $R_1$ is a hydrogen atom, $R_2$ is a group of the formula,

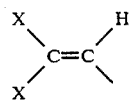

(in which X is a methyl group, a chlorine, bromine or fluorine atom), and when $R_1$ is a methyl group, $R_2$ is a methyl group; and Y is a 1-methyl-2-propenyl, 1-methyl-2-propynyl, 2-cyclopentenyl or 2-cyclohexenyl group, and their production and use as an insecticide.

3 Claims, No Drawings

CYCLOPROPANECARBOXYLATES, THEIR PRODUCTION AND INSECTICIDE CONTAINING THEM AS AN ACTIVE INGREDIENT

This application is a continuation of application Ser. No. 306,376, filed Sept. 28, 1981, now abandoned.

The present invention relates to novel carboxylic acid esters of the formula (I), a method for producing such esters and an insecticidal composition containing said esters as active ingredient.

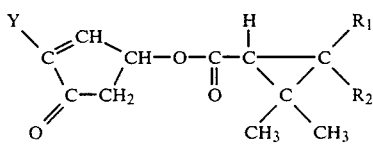

wherein $R_1$ is a hydrogen atom or a methyl group, and when $R_1$ is a hydrogen atom, $R_2$ is a group of the formula,

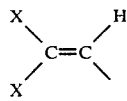

(in which X is a methyl group, a chlorine, bromine or fluorine atom), and when $R_1$ is a methyl group, $R_2$ is a methyl group; and Y is a 1-methyl-2-propenyl, 1-methyl-2-propynyl, 2-cyclopentenyl or 2-cyclohexenyl group.

Various kinds of cyclopropanecarboxylic acid ester type insecticides are known, and some of such insecticides are found in the list of the pyrethrum compositions. Among many currently used insecticides, those of the pyrethrum compositions are widely used for controlling the sanitary harmful insects and the harmful insects in agriculture and horticulture because of their many advantageous properties such as low toxicity to man and beast, rapid effect on the harmful insects and unlikeliness of making the harmful insects resistant to them in addition to their inherent insecticidal activity. These pyrethrum insecticides, however, have drawbacks that they are expensive and subject to certain restrictions in the scope of their applications, and hence a plurality of analogous compounds have been synthesized by many scientists. But very few of them are superior to natural pyrethrin or allethrin from the overall aspect of wide application, efficacy and cost.

What is most important to insect controlling agents is to rapidly knock down and kill insects aimed at, thereby preventing damages by the insects.

As a result of a study of search for insecticides having the foregoing desirable characteristics, the inventors found that the novel carboxylic acid ester of the formula (I),

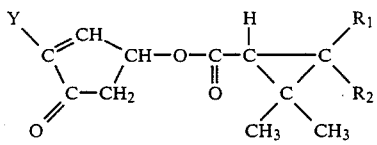

wherein $R_1$ is a hydrogen atom or a methyl group, and when $R_1$ is a hydrogen atom, $R_2$ is a group of the formula,

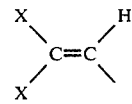

(in which X is a methyl group, a chlorine, bromine or fluorine atom), and when $R_1$ is a methyl group, $R_2$ is a methyl group; and Y is a 1-methyl-2-propenyl, 1-methyl-2-propynyl, 2-cyclopentenyl or 2-cyclohexenyl group, preferably 1-methyl-2-propenyl group, has excellent knock-down and lethal effects against harmful insanitary insects and can be synthesized easily. Further, the inventors confirmed that this novel compound is applicable to practical use, and thus attained to the present invention.

A synthetic method for this ester will be illustrated below.

The ester of the formula (I) is obtained by reacting a cyclopentenolone of the formula (II),

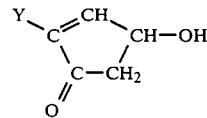

wherein Y is as defined above, with a carboxylic acid of the formula (III),

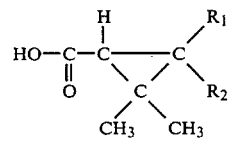

wherein $R_1$ and $R_2$ are as defined above, or its reactive derivative in the presence of a suitable reaction assistant, if necessary. The reactive derivative referred to herein means acid halides, (mixed) acid anhydrides and the like.

Referring to this synthetic method in more detail, it is a method of obtaining the ester of the formula (I) by reacting the alcohol of the formula (II) with the carboxylic acid of the formula (III) or its acid halide or acid anhydride (mixed acid anhydrides).

When the acid itself is used, the reaction is achieved under dehydration condition. That is, the ester of the formula (I) can be obtained by reacting the alcohol of the formula (II) with the carboxylic acid of the formula (III) in a solvent at from 0° C. to the boiling point of the solvent in the presence of a dehydrating agent such as dicyclohexylcarbodiimide. The solvent includes for example benzene, toluene, petroleum ether and chloroform.

The reaction time is generally 1 to 24 hours, and the amounts of the carboxylic acid of the formula (III) and the dehydrating agent used are generally 1.0 to 1.5 times by mole and 1.0 to 2.0 times by mole, respectively, based on the alcohol of the formula (II).

When the acid halide is used, the objective ester is obtained by reaction with the alcohol of the formula (II) using organic tertiary bases such as pyridine or triethylamine as acid-binding agent.

In this reaction, any acid halide within the scope of this invention can be used, but the acid chloride is generally used. The use of solvents is favorable to allow the reaction to proceed smoothly, and solvents such as benzene, toluene and petroleum benzine are generally used. The reaction time and reaction temperature commonly employed are 10 minutes to 24 hours and 0° C. to 60° C., respectively. The amounts of the acid halide and organic tertiary base used are generally 1.0 to 1.5 times by mole and 1.0 to 3.0 times by mole, respectively, based on the alcohol of the formula (II).

When the acid anhydride is used, the object is achieved by reaction with the alcohol of the formula (II) at room temperature without special necessity for reaction assistants. Heating is favorable for promoting the reaction, and the use of solvents (e.g. toluene, benzene) and organic tertiary bases (e.g. pyridine, triethylamine) is favorable for allowing the reaction to proceed smoothly, but these are not essential. The reaction temperature is from 0° C. to the boiling point of the solvent, and the reaction time is 10 minutes to 24 hours. The amount of the acid anhydride used is generally 1.0 to 1.5 times by mole based on the alcohol of the formula (II).

Examples of compounds thus synthesized will be shown in the following table but the compounds of the present invention are not of course limited to these examples.

TABLE 1

(I)

| Compound No. | Chemical structure* Y | $R_1$ | $R_2$ | Physical property | Alcohol moiety | Acid moiety |
|---|---|---|---|---|---|---|
| (1) | $CH_2=CH-CH(CH_3)-$ | H | $-CH=C(CH_3)_2$ | $n_D^{20.0}$ 1.5042 | (±) | (±)-cis, trans |
| (2) | " | H | $-CH=CCl_2$ | $n_D^{17.5}$ 1.5268 | (±) | (±)-cis, trans |
| (3) | " | $-CH_3$ | $-CH_3$ | m.p. 51–52° C. | (±) | — |
| (4) | " | H | $-CH=CF_2$ | $n_D^{23.5}$ 1.4903 | (±) | (±)-cis, trans |
| (5) | " | H | $-CH=CBr_2$ | $n_D^{20.5}$ 1.5565 | (±) | (±)-cis |
| (6) | " | H | $-CH=C(CH_3)_2$ | $n_D^{17.5}$ 1.5061 | (±) | (±)-trans |
| (7) | " | H | $-CH=CCl_2$ | $n_D^{21.5}$ 1.5281 | (±) | (±)-cis |
| (8) | " | H | $-CH=C(CH_3)_2$ | $n_D^{20.0}$ 1.5055 | (±) | (±)-cis, trans (cis/trans = 2/8) |
| (9) | $CH\equiv C-CH(CH_3)-$ | H | $-CH=C(CH_3)_2$ | $n_D^{27.5}$ 1.5034 | (±) | (±)-cis, trans |
| (10) | " | H | $-CH=CCl_2$ | $n_D^{28.5}$ 1.5237 | (±) | (±)-cis, trans |
| (11) | " | $-CH_3$ | $-CH_3$ | $n_D^{25.5}$ 1.5053 | (±) | — |

TABLE 1-continued $$\text{(I)}$$

Structure (I): Y-substituted cyclopentenone ester with cyclopropane bearing $R_1$, $R_2$, and two $CH_3$ groups.

| Compound No. | Y | $R_1$ | $R_2$ | Physical property | Alcohol moiety | Acid moiety |
|---|---|---|---|---|---|---|
| (12) | " | H | $-CH=C(F)(F)$ | $n_D^{26.5}$ 1.4889 | (±) | (±)-cis, trans |
| (13) | " | H | $-CH=C(Br)(Br)$ | $n_D^{26.5}$ 1.5545 | (±) | (±)-cis |
| (14) | " | H | $-CH=C(CH_3)(CH_3)$ | $n_D^{26.5}$ 1.5040 | (±) | (±)-trans |
| (15) | " | H | $-CH=C(Cl)(Cl)$ | $n_D^{23.5}$ 1.5242 | (±) | (±)-cis |
| (16) | " | H | $-CH=C(CH_3)(CH_3)$ | $n_D^{27.5}$ 1.5031 | (±) | (±)-cis, trans (cis/trans = 2/8) |
| (17) | cyclopent-2-enyl | H | $-CH=C(CH_3)(CH_3)$ | $n_D^{28.5}$ 1.5142 | (±) | (±)-trans |
| (18) | " | H | $-CH=C(Cl)(Cl)$ | $n_D^{28.5}$ 1.5356 | (±) | (±)-cis, trans |
| (19) | " | $-CH_3$ | $-CH_3$ | $n_D^{27.0}$ 1.5034 | (±) | — |
| (20) | " | H | $-CH=C(F)(F)$ | $n_D^{28.0}$ 1.4919 | (±) | (±)-cis, trans |
| (21) | cyclohex-2-enyl | H | $-CH=C(Br)(Br)$ | $n_D^{27.5}$ 1.5584 | (±) | (±)-cis |
| (22) | " | H | $-CH=C(CH_3)(CH_3)$ | $n_D^{27.5}$ 1.5169 | (±) | (±)-cis, trans |
| (23) | " | H | $-CH=C(Cl)(Cl)$ | $n_D^{25.5}$ 1.5369 | (±) | (±)-cis |
| (24) | cyclopent-2-enyl | H | $-CH=C(CH_3)(CH_3)$ | $n_D^{27.5}$ 1.5155 | (±) | (±)-cis, trans (cis/trans = 2/8) |

*Explanation of symbols, Y, $R_1$ and $R_2$, in the structure represented by the above formula (I).

The production of the carboxylic acid esters of the present invention will be illustrated in more detail with reference to the following synthetic examples.

EXAMPLE 1

[Synthesis of Compound No. (1)]

($\pm$)-4-Hydroxy-2-(1-methyl-2-propenyl)-2-cyclopenten-1-one (1.52 g) and pyridine (1.2 g) were dissolved in toluene (20 ml), and ($\pm$)-cis,trans-chrysanthemic acid chloride (1.86 g) was added at 20° C., followed by stirring for 5 hours at the same temperature. The reaction solution was washed successively with 5% HCl, aqueous sodium hydrogen carbonate solution and aqueous sodium chloride solution, and then dried over magnesium sulfate. After removing the solvent by evaporation, the residue was chromatographed on a column of silica gel to obtain 2.36 g of a pale yellow oil.

EXAMPLE 2

[Synthesis of Compound No. (2)]

($\pm$)-4-Hydroxy-2-(1-methyl-2-propenyl)-2-cyclopenten-1-one (1.52 g) and pyridine (1.2 g) were dissolved in toluene (20 ml), and ($\pm$)-cis,trans-3-(2,2-dichlorovinyl)-2,2-dimethylcyclopropane-1-carboxylic acid chloride (2.20 g) was added at 0° C. After stirring at 30° C. for 10 hours, the reaction solution was treated in the same manner as in Example 1, and then purified by column chromatography to obtain 2.78 g of a pale yellow oil.

EXAMPLE 3

[Synthesis of Compound No. (6)]

($\pm$)-4-Hydroxy-2-(1-methyl-2-propenyl)-2-cyclopenten-1-one (1.52 g) and (+)-trans-chrysanthemic acid (1.68 g) were dissolved in chloroform (30 ml), and dicyclohexylcarbodiimide (2.5 g) was added with stirring, followed by stirring at 20° C. for 10 hours. The reaction solution was then filtered, concentrated and chromatographed on a column of silica gel to obtain 2.27 g of a pale yellow oil.

EXAMPLE 4

[Synthesis of Compound No. (3)]

($\pm$)-4-Hydroxy-2-(1-methyl-2-propenyl)-2-cyclopenten-1-one (1.52 g) was dissolved in a mixture of toluene (20 ml) and triethylamine (1.5 g), and 2,2,3,3-tetramethylcyclopanecarboxylic acid anhydride (2.70 g) was added, followed by refluxing for 3 hours. After cooling, the reaction solution was washed successively with water, aqueous sodium hydrogen carbonate solution and aqueous sodium chloride solution, and then concentrated to remove toluene. The residue was purified by chromatography on a column of silica gel to obtain 2.30 g of a pale yellow oil.

EXAMPLE 5

[Synthesis of Compound No. (9)]

Procedure was carried out in completely the same manner as in Example 1 except that ($\pm$)-4-hydroxy-2-(1-methyl-2-propynyl)-2-cyclopenten-1-one (1.50 g) was used in place of ($\pm$)-4-hydroxy-2-(1-methyl-2-propenyl)-2-cyclopenten-1-one, to obtain 2.10 g of a pale yellow oil.

EXAMPLE 6

[Synthesis of Compound No. (10)]

Procedure was carried out in completely the same manner as in Example 2 except that ($\pm$)-4-hydroxy-2-(1-methyl-2-propynyl)-2-cyclopenten-1-one (1.50 g) was used in place of ($\pm$)-4-hydroxy-2-(1-methyl-2-propenyl)-2-cyclopenten-1-one, to obtain 2.30 g of a pale yellow oil.

EXAMPLE 7

[Synthesis of Compound No. (14)]

Procedure was carried out in completely the same manner as in Example 3 except that ($\pm$)-4-hydroxy-2-(1-methyl-2-propynyl)-2-cyclopenten-1-one (1.50 g) was used in place of ($\pm$)-4-hydroxy-2-(1-methyl-2-propenyl)-2-cyclopenten-1-one, to obtain 2.00 g of a pale yellow oil.

EXAMPLE 8

[Synthesis of Compound No. (11)]

Procedure was carried out in completely the same manner as in Example 4 except that ($\pm$)-4-hydroxy-2-(1-methyl-2-propynyl)-2-cyclopenten-1-one (1.50 g) was used in place of ($\pm$)-4-hydroxy-2-(1-methyl-2-propenyl)-2-cyclopenten-1-one, to obtain 1.98 g of a pale yellow oil.

EXAMPLE 9

[Synthesis of Compound No. (17)]

Procedure was carried out in completely the same manner as in Example 1 except that ($\pm$)-4-hydroxy-2-(2-cyclopentenyl)-2-cyclopenten-1-one (1.64 g) and (+)-trans-chrysanthemic acid chloride (1.86 g) were used in place of ($\pm$)-4-hydroxy-2-(1-methyl-2-propenyl)-2-cyclopenten-1-one and ($\pm$)-cis,trans-chrysanthemic acid chloride, respectively. Thus, 2.40 g of a pale yellow oil was obtained.

EXAMPLE 10

[Synthesis of Compound No. (18)]

Procedure was carried out in completely the same manner as in Example 2 except that ($\pm$)-4-hydroxy-2-(2-cyclopentenyl)-2-cyclopenten-1-one (1.64 g) was used in place of ($\pm$)-4-hydroxy-2-(1-methyl-2-propenyl)-2-cyclopenten-1-one, to obtain 2.75 g of a pale yellow oil.

EXAMPLE 11

[Synthesis of Compound No. (22)]

Procedure was carried out in completely the same manner as in Example 3 except that ($\pm$)-4-hydroxy-2-(2-cyclohexenyl)-2-cyclopenten-1-one (1.78 g) and (+)-cis,trans-chrysanthemic acid (1.68 g) were used in place of ($\pm$)-4-hydroxy-2-(1-methyl-2-propenyl)-2-cyclopenten-1-one and (+)-trans-chrysanthemic acid, respectively. Thus, 2.35 g of a pale yellow oil was obtained.

EXAMPLE 12

[Synthesis of Compound No. (23)]

Procedure were carried out in completely the same manner as in Example 4 except that ($\pm$)-4-hydroxy-2-(2-cyclohexenyl)-2-cyclopenten-1-one (1.78 g) and (+)-cis-2,2-dimethyl-3-(2,2-dichlorovinyl)cyclopropanecarboxylic acid anhydride (4.0 g) were used in place of (±)-4-hydroxy-2-(1-methyl-2-propenyl)-2-cyclopenten-1-one and 2,2,3,3-tetramethylcyclopropanecarboxylic acid anhydride, respectively. Thus, 2.40 g of a pale yellow oil was obtained.

The alcohol of the formula (II), an alcohol moiety of the carboxylic acid esters of the present invention, is a novel compound, and it can easily be synthesized in high yields, as shown by the following reaction process.

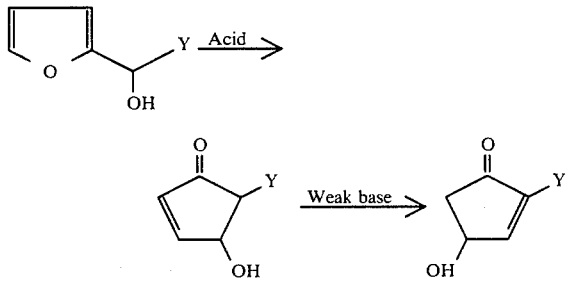

wherein Y is as defined above, by reacting a furfural with the Grignard reagent of 3-halo-1-butene, 1-halo-2-butene, 3-halo-1-butyne, 3-chloro-1-cyclopentene or 3-chloro-1-cyclohexene, and reacting the resulting 2-furyl-carbinol derivative with an acid in the presence of water and a polar solvent to obtain 2-substituted-3-hydroxy-4-cyclopentenone as intermediate which is then isomerized with a weak base catalyst.

REFERENCE EXAMPLE 1

Synthesis of (±)-4-hydroxy-2-(1-methyl-2-propenyl)-2-cyclopenten-1-one (1) Synthesis of 1-(2-furyl)-2-methyl-3-buten-1-ol Magnesium (36 g, 1.5 mole) and tetrahydrofuran (THF) (300 ml) were added to a reactor, and a solution of crotyl chloride or 3-chloro-1-butene (118 g, 1.8 mole) in THF (100 ml) was added dropwise at 30° to 35° C. to prepare a Grignard reagent. Thereafter, to this THF solution of the Grignard reagent was added dropwise a solution of furfural (106 g, 1.1 mole) in THF (150 ml) at 20° to 30° C. over about 1 hour, followed by stirring at room temperature for further 2 hours. After completion of the reaction, the reaction solution was poured into an aqueous ammonium chloride solution (about 500 ml), followed by extraction with ether. The ether extract was washed with water, dried and concentrated, and the residue obtained was distilled under reduced pressure to obtain 150 g (yield, 90%) of pure 1-(2-furyl)-2-methyl-3-buten-1-ol having a boiling point of 95°–107° C./25 mmHg.

(2) Synthesis of (±)-3-hydroxy-2-(1-methyl-2-propenyl)-4-cyclopenten-1-one 1-(2-Furyl)-2-methyl-3-buten-1-ol (122 g, 0.8 mole) was dissolved in a 2:1 mixture (1.2 liter) of acetone and water in a reactor, and polyphosphoric acid (20 g) was then added. Thereafter, reaction was carried out at 50° to 60° C. for about 48 hours with stirring. After completion of the reaction, the reaction solution was cooled and neutralized with addition of a saturated aqueous solution (200 ml) of sodium hydrogen carbonate, followed by extraction with a solvent. The extract was washed with water, dried and concentrated. The residue obtained was distilled under reduced pressure to obtain 74 g (yield, 61%) of pure (±)-3-hydroxy-2-(1-methyl-2-propenyl)-4-cyclopenten-1-one having a boiling point of 122°–130° C./3 mmHg.

(3) Synthesis of (±)-4-hydroxy-2-(1-methyl-2-propenyl)-2-cyclopenten-1-one

A column for chromatography was packed with active alumina for chromatography (500 g), and benzene and then 2-(1-methyl-2-propenyl)-3-hydroxy-4-cyclopenten-1-one (50 g, 0.2 mole) were poured therein, followed by standing at room temperature for 24 hours. Thereafter, (±)-4-hydroxy-2-(1-methyl-2-propenyl)-2-cyclopenten-1-one was eluted from alumina with ethyl acetate until adsorption of the compound to alumina was no longer detectable. Ethyl acetate and benzene were removed by evaporation, and the residue obtained was distilled under reduced pressure to obtain 47.5 g (yield, 95%) of pure (±)-4-hydroxy-2-(1-methyl-2-propenyl)-2-cyclopentene-1-one. Boiling point: 109°–121° C./3 mmHg.

REFERENCE EXAMPLE 2

Synthesis of (±)-4-hydroxy-2-(1-methyl-2-propynyl)-2-cyclopenten-1-one (1) Synthesis of 1-(2-furyl)-2-methyl-3-butyn-1-ol Aluminum (5.0 g, 0.18 mole), mercuric chloride (100 mg) and tetrahydrofuran (THF) (70 ml) were added to a reactor, and a solution of 3-bromo-1-butyne (20 g, 0.15 mole) in THF (20 ml) was added dropwise at 40° to 50° C. to prepare a Grignard reagent. Thereafter, to this THF solution of the Grignard reagent was added dropwise a solution of furfural (11.5 g, 0.12 mole) in THF (20 ml) at 20° to 30° C. over about 1 hour, followed by stirring at room temperature for further 2 hours. After completion of the reaction, the reaction solution was poured into an aqueous ammonium chloride solution (about 100 ml) and extracted with ether. The extract was washed with water, dried and concentrated. The residue obtained was distilled under reduced pressure to obtain 10.4 g (yield, 58%) of pure 1-(2-furyl)-2-methyl-3-butyn-1-ol having a boiling point of 75°–85° C./3 mmHg.

(2) Synthesis of (±)-3-hydroxy-2-(1-methyl-2-propynyl)-4-cyclopenten-1-one 1-(2-Furyl)-2-methyl-3-butyn-1-ol (15 g, 0.1 mole) was dissolved in a 2:1 mixture (150 ml) of acetone and water in a reactor, and p-toluenesulfonic acid (3 g) was dried. Thereafter, reaction was carried out at 50° to 60° C. for about 48 hours with stirring. After completion of the reaction, the reaction solution was cooled and neutralized with addition of a saturated aqueous solution (30 ml) of sodium hydrogen carbonate, followed by extraction with a solvent. The extract was washed with water, dried and concentrated. The residue obtained was distilled under reduced pressure to obtain 7.8 g (yield, 52%) of pure (±)-3-hydroxy-2-(1-methyl-2-propynyl)-4-cyclopenten-1-one having a boiling point of 110°–115° C./3 mmHg.

(3) Synthesis of (±)-4-hydroxy-2-(1-methyl-2-propynyl)-2-cyclopenten-1-one

A column for chromatography was packed with active alumina for chromatography (500 g), and benzene and then (±)-3-hydroxy-2-(1-methyl-2-propynyl)-4-cyclopenten-1-one (30 g, 0.2 mole) were poured therein, followed by standing at room temperature for 24 hours. Thereafter, (±)-4-hydroxy-2-(1-methyl-2-propynyl)-2-cyclopenten-1-one was eluted from alumina with ethyl acetate until adsorption of the compound to alumina was no longer detectable. Ethyl acetate and benzene were removed by evaporation, and the residue obtained was distilled under reduced pressure to obtain 24.9 g (yield, 83%) of pure (±)-4-hydroxy-2-(1-methyl-2-propynyl)-2-cyclopenten-1-one. Boiling point: 125°–131° C./3 mmHg.

REFERENCE EXAMPLE 3

Synthesis of (±)-4-hydroxy-2-(2-cyclopentenyl)-2-cyclopenten-1-one (1) Synthesis of 2-cyclopentenyl-2-furyl methanol Magnesium (36 g, 1.5 mole) and tetrahydrofuran (THF) (300 ml) were added to a reactor, and a solution of 3-chloro-1-cyclopentene (184.5 g, 1.8 mole) in THF (200 ml) was added dropwise at 0° to 10° C. to prepare a Grignard reagent. Thereafter, to this THF solution of the Grignard reagent was added dropwise a solution of furfural (106 g, 1.1 mole) in THF (150 ml) at 0° to 10° C. over about 1 hour, followed by stirring at 20° C. for further 2 hours. After completion of the reaction, the reaction solution was poured into an aqueous ammonium chloride solution (about 1 liter), followed by extraction with ether. The extract was washed with water, dried and concentrated. The residue obtained was distilled under reduced pressure to obtain 135 g (yield, 75%) of pure 2-cyclopentenyl-2-furyl methanol having a boiling point of 80°–86° C./3 mmHg.

(2) Synthesis of (±)-3-hydroxy-2-(2-cyclopentenyl)-4-cyclopenten-1-one

2-Cyclopentenyl-2-furyl methanol (131 g, 0.8 mole) was dissolved in a 2:1 mixture (1.5 liters) of acetone and water in a reactor, and polyphosphoric acid (20 g) was added thereto. Thereafter, reaction was carried out at 50° to 60° C. for about 24 hours with stirring. After completion of the reaction, the reaction solution was cooled and neutralized with addition of a saturated aqueous solution (200 ml) of sodium hydrogen carbonate, followed by extraction with a solvent. The extract was washed with water, dried and concentrated. The residue obtained was distilled under reduced pressure to obtain 72 g (yield, 55%) of pure (±)-3-hydroxy-2-(2-cyclopentenyl)-4-cyclopenten-1-one having a boiling point of 115°–120° C./3 mmHg.

(3) Synthesis of (±)-4-hydroxy-2-(2-cyclopentenyl)-2-cyclopenten-1-one

A column for chromatography was packed with active alumina for chromatography (500 g), and benzene and then (±)-3-hydroxy-2-(2-cyclopentenyl)-4-cyclopenten-1-one (32.8 g, 0.2 mole) were poured therein, followed by standing at room temperature for 24 hours. Thereafter, (±)-4-hydroxy-2-(2-cyclopentenyl)-2-cyclo-penten-1-one was eluted from alumina with ethyl acetate until adsorption of the compound to alumina was no longer detectable. Ethyl acetate and benzene were removed by evaporation, and the residue obtained was distilled under reduced pressure to obtain 29.8 g (yield, 91%) of pure (±)-4-hydroxy-2-(2-cyclopentenyl)-2-cyclopenten-1-one. Boiling point: 115°–119° C./2 mmHg.

REFERENCE EXAMPLE 4

Synthesis of (±)-4-hydroxy-2-(2-cyclohexenyl)-2-cyclopenten-1-one

In the same manner as in Reference example 3, 95 g of 3-hydroxy-2-(2-cyclohexenyl)-4-cyclopenten-1-one (yield, 66.7%; boiling point, 118°–123° C./0.5 mmHg) was obtained from 142 g of 2-cyclohexenyl-2-furyl methanol, and then 30.4 g of (±)-4-hydroxy-2-(2-cyclohexenyl)-2-cyclopenten-1-one (yield, 85.4%; boiling point, 145°–147° C./1.5 mmHg) was obtained from 35.6 g of said (±)-3-hydroxy-2-(2-cyclohexenyl)-4-cyclopenten-1-one.

In producing an insecticide using the present compounds (I), the compounds may be formulated, like the conventional pyrethroids, into optional preparation forms using diluents for the common insecticides according to the methods well known to those skilled in the art. The preparation forms include for example emulsifiable concentrates, wettable powders, dusts, granules, fine granules, oil sprays, aerosols, heating fumigants (mosquito coils, electric mosquito fumigators), foggings, non-heating fumigants, baits of powder form or solid form containing attractants and other optional forms. And the present compounds can be applied to various uses in required preparation forms and using required carriers. Also, the insecticidal activity of the present compounds can be increased by blending with synergists for pyrethroids or other well-known effective synergists for Allethrin and Pyrethrin. The synergists for pyrethroids include for example α-[2-(2-butoxyethoxy)ethoxy]-4,5-methylenedioxy-2-propyltoluene (hereinafter referred to as piperonylbutoxide), 1,2-methylenedioxy-4-[2-(octylsulfinyl)propyl]benzene (hereinafter referred to as sulfoxide), 4-(3,4-methylenedioxyphenyl)-5-methyl-1,3-dioxane (hereinafter referred to as sufloxane), N-(2-ethylhexyl)-bicyclo[2,2,1]hepta-5-ene-2,3-dicarboximide (hereinafter referred to as MGK-264), octachlorodipropyl ether (hereinafter referred to as S-421) and isobornylthiocyanoacetate (hereinafter referred to as Thanite).

In general, carboxylic esters tend to be inferior in resistance to light, heat and oxidation, and therefore compositions of more stable effect can be obtained by adding a proper amount of stabilizers. The stabilizers include for example antioxidants and ultraviolet absorbers such as phenol derivatives (e.g. BHT, BHA), bisphenol derivatives, arylamines (e.g. phenyl-α-naphthylamine, phenyl-β-naphthylamine, condensation products of phenetidine and acetone), and benzophenone compounds.

Further, multi-purpose compositions of excellent efficacy can be produced by mixing with other active ingredients for example Allethrin, N-(chrysanthemoxymethyl)-3,4,5,6-tetrahydrophthalimide (hereinafter referred to as tetramethrin), 5-benzyl-3-furylmethyl chrysanthemate (hereinafter referred to as resmethrin), 3-phenoxybenzyl chrysanthemate (hereinafter referred to as phenothrin), 5-propargylfurfuryl chrysanthemate, 2-methyl-5-propargyl-3-furylmethyl chrysanthemate, d-trans or di-cis.trans isomers of these chrysanthemates, pyrethrum extracts, d-trans or d-cis.trans chrysanthemic esters of d-allethrolone, and other well-known cyclopropanecarboxylic esters; organophosphorus insecticides such as O,O-dimethyl O-(3-methyl-4-nitrophenyl)phosphorothioate (hereinafter referred to as fenitrothion), O,O-dimethyl O-4-cyanophenylphosphorothioate (hereinafter referred to as Cyanophos), O,O-dimethyl O-(2,2-dichlorovinyl)phosphate (hereinafter referred to as dichlorvos); carbamate insecticides such as 1-naphthyl N-methylcarbamate, 3,4-dimethylphenyl N-methylcarbamate (hereinafter referred to as MPMC); other insecticides, fungicides, nematocides, acaricides, plant growth regulators, fertilizers, microbial pesticides such as B.T. and B.M., insect hormone compound and other agricultural chemicals. Further, a synergistic effect can be expected by such mixing.

The foregoing preparations generally contain 0.05 to 95.0% by weight, preferably 0.1 to 80.0% by weight, of the active ingredient (including other ingredients mixed). Since, however, the amount and concentration of the active ingredient depend upon the preparation forms, application time, application techniques, application sites, diseases and crops, they may properly be increased or decreased irrespective of the aforesaid ranges.

Next, the preparation and effect of the insecticides of the present invention will be illustrated with reference to the following preparation examples and test examples.

PREPARATION EXAMPLE 1

0.2 Part of each of the present compounds (1) to (24) is dissolved in kerosene and made up to 100 parts with kerosene to obtain the oil spray of each compound.

PREPARATION EXAMPLE 2

To 0.1 part of each of the present compounds (2), (3), (4), (6), (7), (8), (10), (11), (16), (18), (20) and (24) is added 0.5 part of piperonyl butoxide, and the mixture is dissolved in kerosene and made up to 100 parts with kerosene to obtain the oil spray of each compound.

PREPARATION EXAMPLE 3

To 20 parts of each of the present compounds (1) to (24) are added 10 parts of an emulsifier (Sorpol 3005X, a registered trade mark of Tōhō Kagaku Co.) and 70 parts of xylene. The mixture is well mixed with stirring to obtain the emulsifiable concentrate of each compound.

PREPARATION EXAMPLE 4

To 5 parts of each of the present compounds (2), (5), (8), (10), (13), (16), (21), (23) and (24) are added 25 parts of S-421 (described above), 15 parts of an emulsifier (Sorpol 3005X, described above) and 55 parts of xylene. The mixture is well mixed with stirring to obtain the emulsifiable concentrate of each compound.

PREPARATION EXAMPLE 5

0.6 Part of each of the present compounds (1), (2), (3), (4), (5), (6), (7), (8), (12), (16), (18), (20) and (24), 3 parts of xylene and 56.4 parts of deodorized kerosene are well mixed to make a solution. The solution is filled in an aerosol container. After attaching a valve portion to the container, 40 parts of a propellant (liquefied petroleum gas) is charged therein under pressure through the valve to obtain the aerosol of each compound.

PREPARATION EXAMPLE 6

0.55 Part of each of the present compounds (2), (3), (8), (10), (11), (16), (17) and (19), 0.05 part of resmethrin (described above), 3 parts of xylene and 56.4 parts of deodorized kerosene are well mixed to make a solution. The solution is filled in an aerosol container. After attaching a valve portion to the container, 40 parts of a propellant (liquefied petroleum gas) is charged therein under pressure through the valve to obtain the aerosol of each compound.

PREPARATION EXAMPLE 7

0.55 Part of each of the present compounds (3), (6), (11), (14), (18) and (24), 0.05 part of resmethrin (described above), 13.4 parts of deodorized kerosene and 1 part of an emulsifier (Atmos 300, a registered trade mark of Atlas Chemical Co.) are mixed and emulsified with addition of 50 parts of pure water. The emulsion is then filled in an aerosol container together with 35 parts of a 3:1 mixture of deodorized butane and deodorized propane to obtain the water-base aerosol of each compound.

PREPARATION EXAMPLE 8

To 0.3 g of each of the present compounds (1) to (17), (19), (20) and (24) is added 0.3 g of BHT, and the mixture is dissolved in 20 ml of methanol. This solution and 99.4 g of a mosquito coil carrier containing Tabu powder, Pyrethrum marc and wood powder in a ratio of 3:5:1, are uniformly mixed with stirring, and then methanol is evaporated. To the residue is added 150 ml of water, and the mixture is well kneaded, shaped and dried to obtain the mosquito coil of each compound.

PREPARATION EXAMPLE 9

To 0.15 g of each of the present compounds (1) to (16), (19) and (24) is added 0.15 g of the di-cis,trans-chrysanthemic ester of Allethrin, and the mixture is dissolved in 20 ml of methanol. This solution and 99.7 g of a mosquito coil carrier (described above) are uniformly mixed with stirring, and then methanol is evaporated. To the residue is added 150 ml of water, and the mixture is well kneaded, shaped and dried to obtain the mosquito coil of each compound.

PREPARATION EXAMPLE 10

To 0.06 g of each of the present compounds (1) to (17), (19), (20) and (24) are added 0.1 g of piperonyl butoxide and 0.05 g of BHT, and the mixture is dissolved in a suitable amount of chloroform. Thereafter, filter paper of 3.5 cm × 1.5 cm × 0.3 cm (thick) is made to uniformly absorb the solution.

Thus, the fibrous fumigant for heating on a hot plate of each compound is obtained.

PREPARATION EXAMPLE 11

Forty parts of each of the present compounds (1) to (24) and 5 parts of an emulsifier (Sorpol 5029-O, a registered trade mark of Tōh/o Kagaku Co.) are well mixed. The mixture is then well mixed with 55 parts of 300-mesh diatomaceous earth while being stirred in a mortar to obtain the wettable powder of each compound.

PREPARATION EXAMPLE 12

Two parts of each of the present compounds (1) to (24) is dissolved in 20 parts of acetone, and 98 parts of 300-mesh talc is added thereto. The mixture is well mixed with stirring, and acetone is removed by evaporation to obtain the dust of each compound.

PREPARATION EXAMPLE 13

To 80 parts of the present compound (1) are added 10 parts of an emulsifier (Sorpol 3005X, described above) and 10 parts of xylene. The mixture is well mixed with stirring to obtain an emulsifiable concentrate.

TEST EXAMPLE 1

The 20% emulsifiable concentrate of each of the present compounds (1) to (24) obtained in Preparation example 3 was diluted 400 times with water (corresponding to 500 ppm of active ingredient).

On the bottom of a polyethylene cup of 5.5 cm in diameter was placed a piece of filter paper of the same size as the bottom, and 0.7 ml of the above dilute liquor was dropped down to the filter paper. Sucrose (30 mg) was placed on the paper as bait. Thereafter, 10 housefly female adults (*Musca domestica*) were liberated in the cup which was then covered with a lid. After 24 hours, the dead and alive were counted to obtain mortality (2 replications).

| Test compound | Mortality (%) | Test compound | Mortality (%) |
|---|---|---|---|
| Present compound (1) | 100 | Present compound (14) | 100 |
| Present compound (2) | 100 | Present compound (15) | 100 |
| Present compound (3) | 100 | Present compound (16) | 100 |
| Present compound (4) | 100 | Present compound (17) | 100 |
| Present compound (5) | 100 | Present compound (18) | 100 |
| Present compound (6) | 100 | Present compound (19) | 100 |
| Present compound (7) | 100 | Present compound (20) | 100 |
| Present compound (8) | 100 | Present compound (21) | 100 |
| Present compound (9) | 100 | Present compound (22) | 100 |
| Present compound (10) | 100 | Present compound (23) | 100 |
| Present compound (11) | 100 | Present compound (24) | 100 |
| Present compound (12) | 100 | No treatment | 0 |
| Present compound (13) | 100 | | |

TEST EXAMPLE 2

The 0.3% mosquito coils of the present compounds (1), (3), (6), (7), (8) and (11) obtained in Preparation example 8 and those of controls were prepared for.

Ten northern house mosquito adults (*Culex pipiens pallens*) were liberated in a (70 cm)$^3$ glass chamber. One gram of each of the above mosquito coils was ignited at the both ends and placed in the glass chamber. The number of knocked-down insects with the lapse of time was counted, and $KT_{50}$ values were obtained according to the probit method. After 30 minutes elapsed, the knocked-down insects were collected, liberated in a cage for observation and given baits. After 24 hours, the dead and alive were counted to obtain mortality (2 replications).

| Test compound | $KT_{50}$ | Mortality (%) |
|---|---|---|
| Present compound (1) | 10'30" | 34 |
| Present compound (3) | 8'30" | 55 |
| Present compound (6) | 8'30" | 65 |
| Present compound (7) | 9'00" | 45 |
| Present compound (8) | 8'40" | 58 |
| Present compound (11) | 10'30" | 34 |
| Allethrin | 11'10" | 16 |
| Tetramethrin | 18'00" | 20 |

TEST EXAMPLE 3

The oil sprays of the present compounds obtained in Preparation example 2 were each sprayed at a rate of 5 ml/about 100 housefly adults (*Musca domestica*) per group, according to the Campbell's turntable method [Soap and Sanitary Chemicals, Vol. 14, No. 6, 119(1938)]. The adults were thus exposed to the descending mist for 10 minutes. By the next day, more than 80% of the houseflies could be killed in any case.

TEST EXAMPLE 4

20 Northern house mosquito adults (*Culex pipiens pallens*) were liberated in a (70 cm)$^3$ glass chamber, and the oil sprays of the present compounds (1) to (16), (17), (18), (20) and (24) obtained in Preparation example 1 were each sprayed, at a rate of 0.7 ml/group of the adults, under 0.8 atmospheric pressure by means of a spray gun. Within 10 minutes after spraying, more than 80% of the adults could be knocked-down, and by the next day, more than 80% could be killed with any oil spray.

TEST EXAMPLE 5

The emulsifiable concentrates of the present compounds (1) to (24) obtained in Preparation example 3 were each diluted 50,000 times with water. Two liters of the dilute liquor was placed in a styrene case of 23 cm × 30 cm × 6 cm (deep) in volume, and about 100 full grown larvae of northern house mosquito (*Culex pipiens pallens*) were liberated therein. By the next day, more than 90% of the larvae could be killed in any case.

TEST EXAMPLE 6

20 Housefly adults (*Musca domestica*) were liberated in a (70 cm)$^3$ glass chamber in which a battery type small electric fan (wing diameter, 13 cm) was placed and driven. The heating fumigants obtained in Preparation example 10 were each placed on a hot plate in the chamber and fumigated. Within 20 minutes after fumigation, more than 80% of the adults could be knocked down.

TEST EXAMPLE 7

The insecticidal activity on housefly adults (*Musca domestica*) of the aerosols obtained in Preparation examples 5, 6 and 7 was tested according to the aerosol test method (Soap and Chemical Specialities, Blue Book, 1965) using a (6 ft)$^3$ Peet Grady's chamber. As a result, with any aerosol, more than 80% of the flies could be knocked down 15 minutes after spraying, and more than 70% of the flies could be killed by the next day.

TEST EXAMPLE 8

Of the dusts obtained in Preparation example 12, those of the present compounds (1), (2), (7), (10), (15), (21), (22) and (23) were each applied, by means of a Bell jar duster, on rice seedlings cultivated in a 180-ml plastic cup at a rate of 3 kg/10 are. After application, the cup was covered with a wire-screen cage, and about 15 adults of carbamate-resistant green rice leafhopper (*Nephotettix cincticeps*) were liberated therein. After 24 hours, the dead and alive were examined.

| Test compound | Mortality (%) | Test compound | Mortality (%) |
|---|---|---|---|
| Present | 100 | Present | 100 |

-continued

| Test compound | Mortality (%) | Test compound | Mortality (%) |
|---|---|---|---|
| compound (1) | | compound (21) | |
| Present compound (2) | 100 | Present compound (22) | 100 |
| Present compound (7) | 100 | Present compound (23) | 100 |
| Present compound (10) | 100 | BPMC* | 57 |
| Present compound (15) | 100 | No treatment | 3 |

TEST EXAMPLE 9

Ten German cockroach adults (5 males and 5 females) (*Blattella germanica*) were liberated in a polyethylene cup of 9 cm in diameter of which the inside wall was coated with a thin layer of vaseline. The cup was covered with 16-mesh nylon gauze, and placed on the bottom of a glass cylinder of 10 cm in inside diameter and 37 cm high. Thereafter, 0.6 ml of each of the oil sprays of the present compounds (18), (20) and (23) obtained in Preparation example 1 was directly sprayed, by means of a spray gun, at the upper end of the cylinder under 0.6 atmospheric pressure. The number of knocked-down insects with the lapse of time was counted, and from the results, KT$_{50}$ (according to the probit method) and mortality after 72 hours were obtained (2 replications).

| Test compound | KT$_{50}$ | Mortality (%) |
|---|---|---|
| Present compound (18) | 5'00" | 85 |
| Present compound (20) | 4'10" | 75 |
| Present compound (23) | 2'40" | 100 |
| Allethrin (control) | 21'00" | 60 |

What is claimed is:
1. A compound of the formula

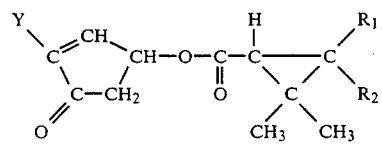

wherein R$_1$ is a hydrogen atom, R$_2$ is a group of the formula,

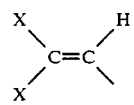

in which X is a methyl group.

2. An insecticidal composition which comprises as an active ingredient an insecticidally effective amount of the compound according to claim 1 and an inert carrier.

3. A method for controlling an insect which comprises applying an insecticidally effective amount of the compound according to claim 1 to the insect.

* * * * *